US008821378B2

(12) United States Patent
Morgenstern Lopez et al.

(10) Patent No.: US 8,821,378 B2
(45) Date of Patent: Sep. 2, 2014

(54) DEVICE AND METHOD FOR MINIMALLY INVASIVE SPINAL INTERVENTION

(75) Inventors: Rudolf Morgenstern Lopez, Esplugues de Llobregat (ES); Wolfgang Ries, Linkenheim (DE)

(73) Assignee: Joimax GmbH, Karlsruhe (DE)

( * ) Notice: Subject to any disclaimer, the term of this patent is extended or adjusted under 35 U.S.C. 154(b) by 893 days.

(21) Appl. No.: 12/516,316

(22) PCT Filed: Nov. 24, 2007

(86) PCT No.: PCT/EP2007/010238
§ 371 (c)(1),
(2), (4) Date: May 26, 2009

(87) PCT Pub. No.: WO2008/064842
PCT Pub. Date: Jun. 5, 2008

(65) Prior Publication Data
US 2011/0184234 A1    Jul. 28, 2011

(30) Foreign Application Priority Data

Nov. 27, 2006   (ES) .................................. 200603026

(51) Int. Cl.
*A61B 17/16* (2006.01)
(52) U.S. Cl.
USPC ............................................. 600/107; 606/79
(58) Field of Classification Search
CPC ....... A61B 1/00; A61B 17/16; A61B 17/1671
USPC ................... 606/79–85, 86 R, 181–185, 190; 623/17.11–17.16; 600/114
See application file for complete search history.

(56) References Cited

U.S. PATENT DOCUMENTS

| 4,625,713 | A |   | 12/1986 | Hiraoka |
| 5,215,526 | A | * | 6/1993  | Deniega et al. .......... 604/164.09 |
| 5,226,426 | A | * | 7/1993  | Yoon .............................. 600/566 |
| 5,406,940 | A |   | 4/1995  | Melzer et al. |
| 5,569,292 | A | * | 10/1996 | Scwemberger et al. ....... 606/185 |
| 5,674,184 | A | * | 10/1997 | Hassler, Jr. ..................... 600/176 |
| 5,792,044 | A | * | 8/1998  | Foley et al. .................... 600/114 |
| 5,797,944 | A | * | 8/1998  | Nobles et al. ................. 606/185 |
| 5,961,522 | A | * | 10/1999 | Mehdizadeh ................... 606/79 |
| 6,228,058 | B1| * | 5/2001  | Dennis et al. ............. 604/164.01 |
| 6,682,535 | B2| * | 1/2004  | Hoogland ....................... 606/80 |
| 6,751,875 | B2| * | 6/2004  | Jones .............................. 30/392 |
| 7,824,327 | B2| * | 11/2010 | Smith ........................... 600/114 |

(Continued)

FOREIGN PATENT DOCUMENTS

| DE | 195 47 246 C1 | 3/1997 |
| DE | 202005016761  | 1/2007 |

(Continued)

*Primary Examiner* — Christopher Beccia
(74) *Attorney, Agent, or Firm* — McGlew and Tuttle, P.C.

(57) ABSTRACT

The invention proposes a device for minimally invasive intervention in the skeletal region, in particular on the spinal column, having at least a cannula with a distal end generally bevelled in shape relative to a symmetrical axis of the cutting tool and an optical probe (endoscope) for insertion through the cavity of the cannula. The device is further characterized in that the cannula takes the form of a hollow cutting tool, in which the most distal region of the distal end comprises a cutting edge, which is incorporated into the edge of the wall of the cutting tool.

78 Claims, 21 Drawing Sheets

(56) References Cited

U.S. PATENT DOCUMENTS

| | | | |
|---|---|---|---|
| 7,922,723 B2* | 4/2011 | Michelson | 606/83 |
| 7,947,058 B2* | 5/2011 | Kahle et al. | 606/190 |
| 7,981,133 B2* | 7/2011 | Chin | 606/190 |
| 2002/0016592 A1 | 2/2002 | Branch et al. | |
| 2002/0052619 A1* | 5/2002 | Transue | 606/185 |
| 2006/0206118 A1* | 9/2006 | Kim et al. | 606/86 |
| 2007/0270898 A1* | 11/2007 | Lillehei | 606/198 |

FOREIGN PATENT DOCUMENTS

| | | |
|---|---|---|
| EP | 0 585 826 | 3/1994 |
| EP | WO 00/76409 | 12/2000 |
| EP | 1 468 652 A1 | 10/2004 |
| WO | WO 2006/044727 | 4/2006 |
| WO | WO 2006/091622 | 8/2006 |
| WO | WO 2007/035892 | 3/2007 |

* cited by examiner

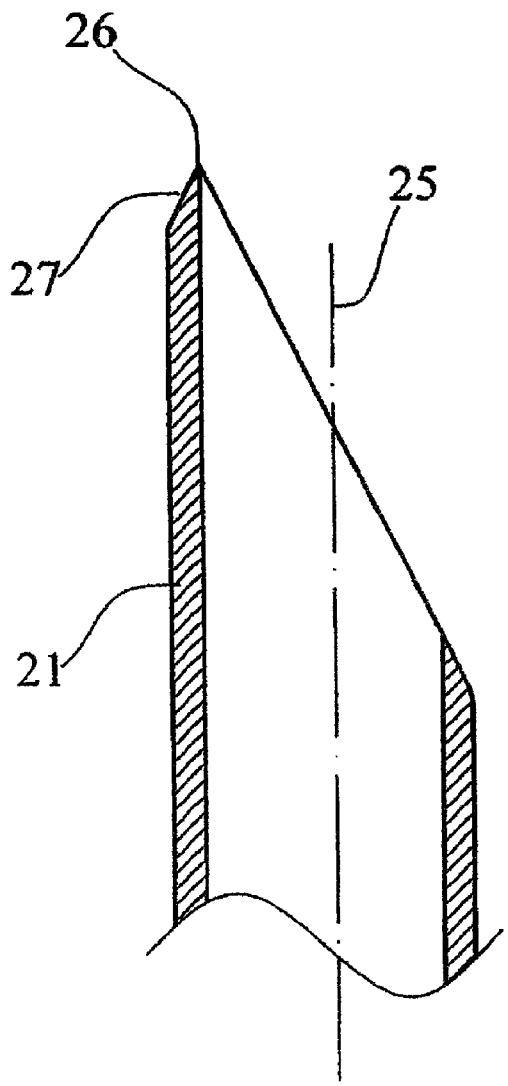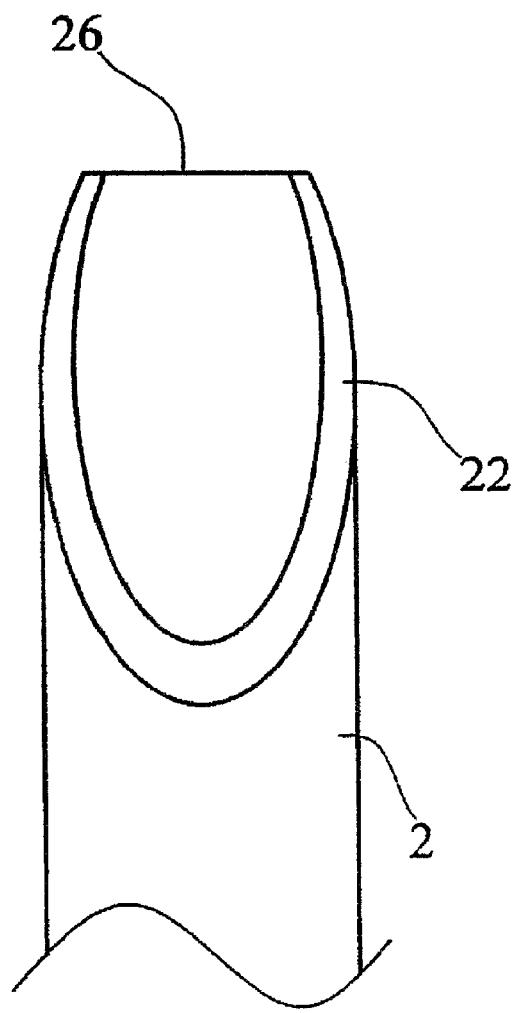
Fig. 3.1    Fig. 3.2

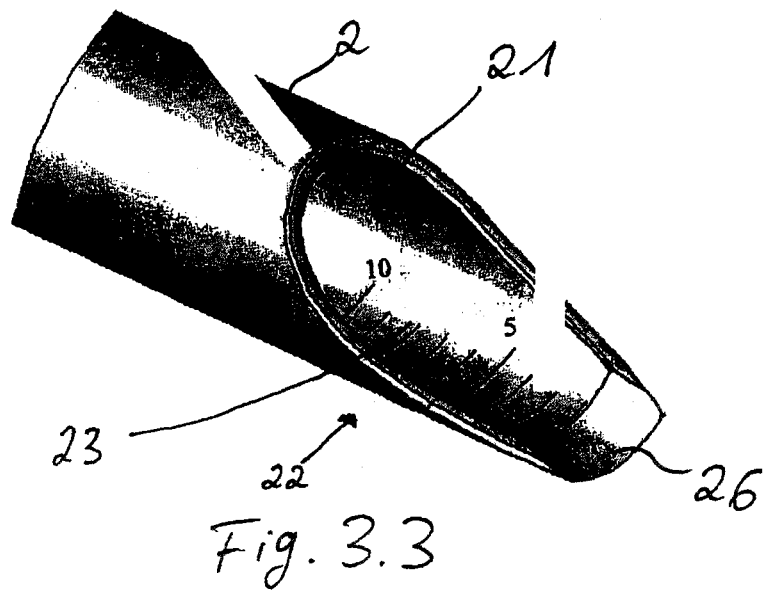
Fig. 3.3
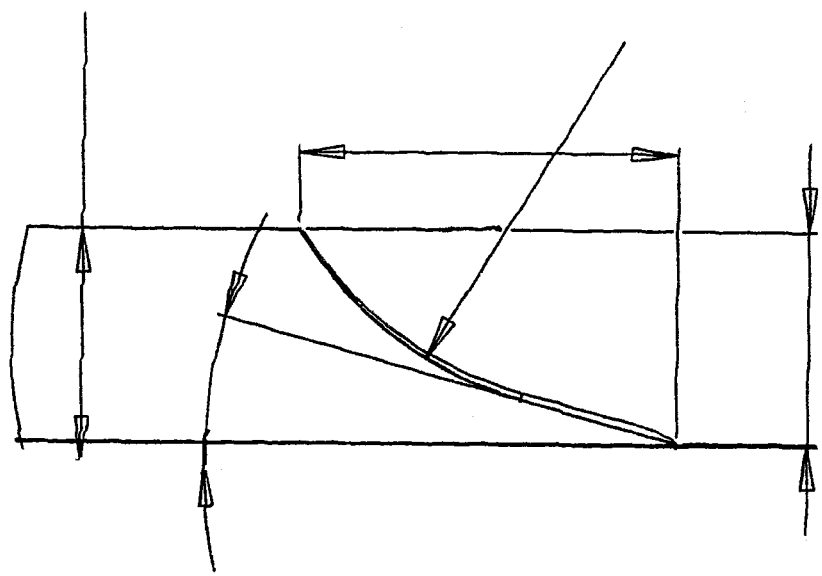
Fig. 3.4

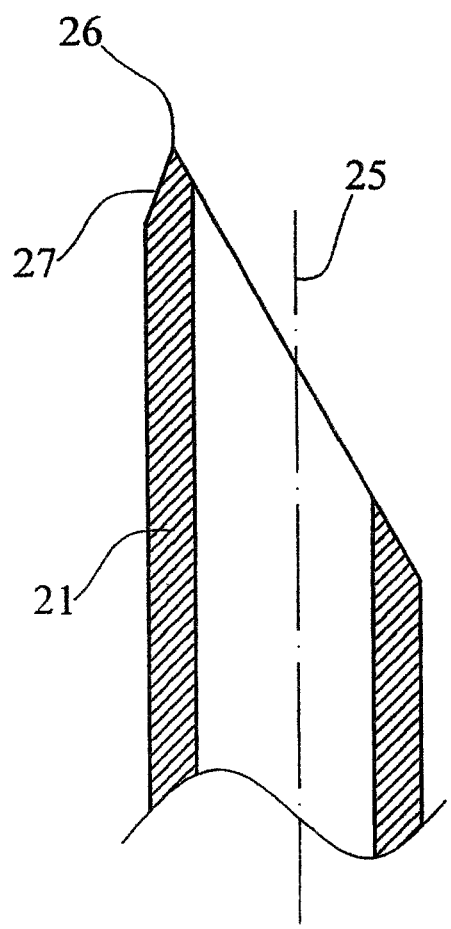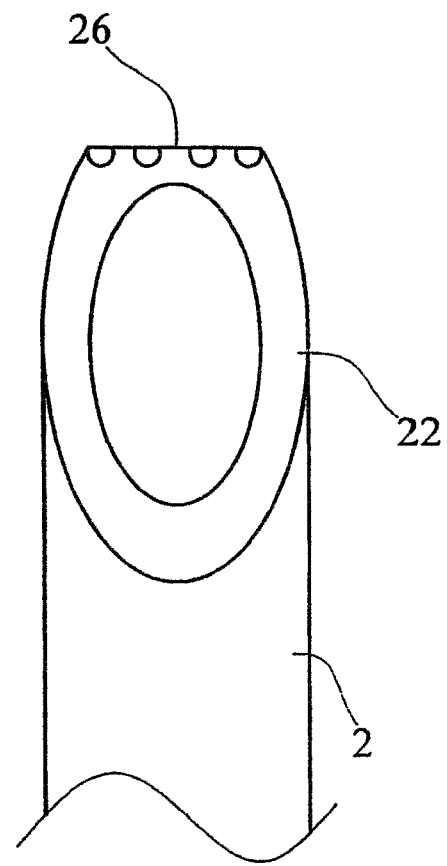
Fig. 5.1  Fig. 5.2

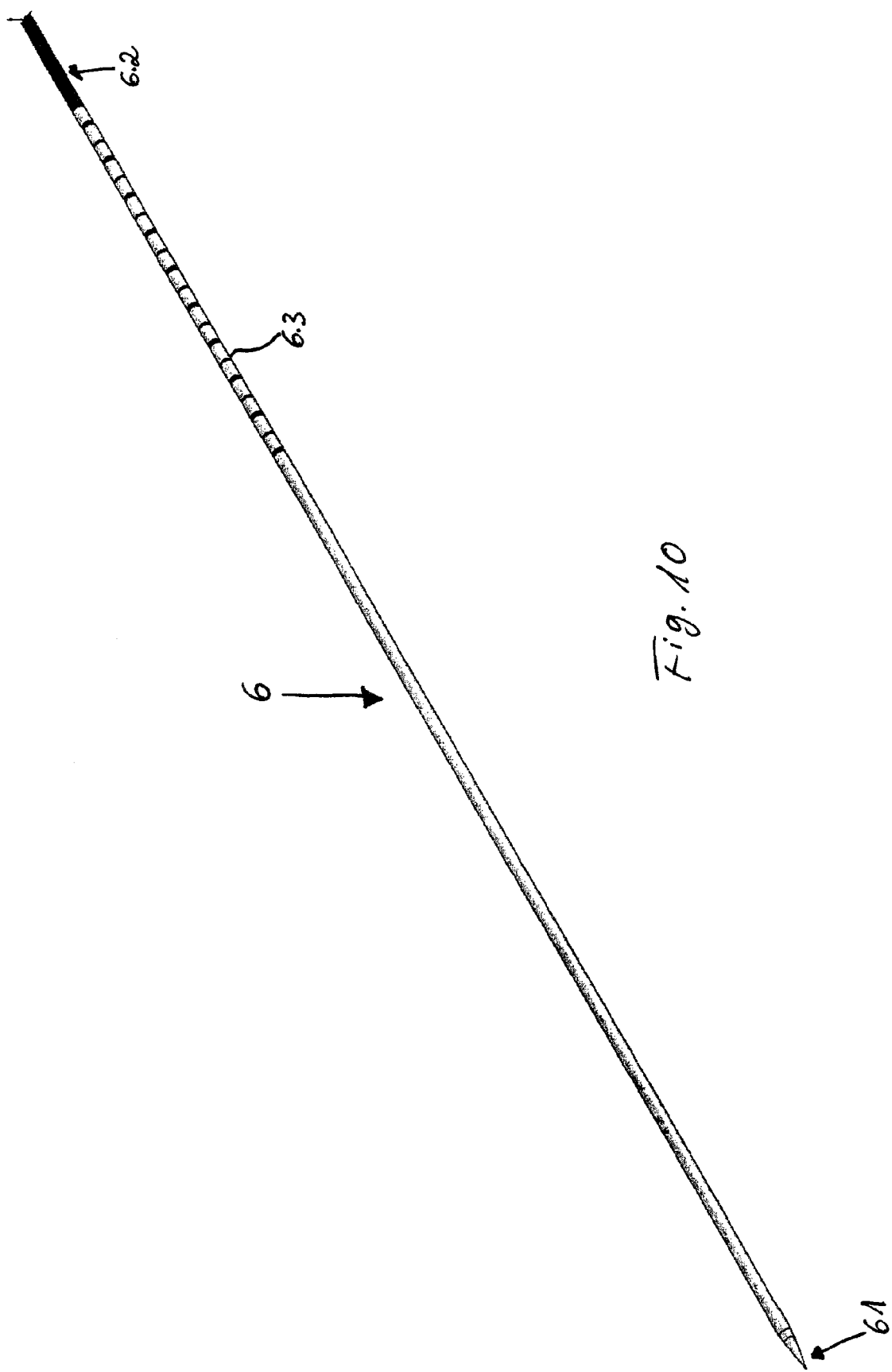

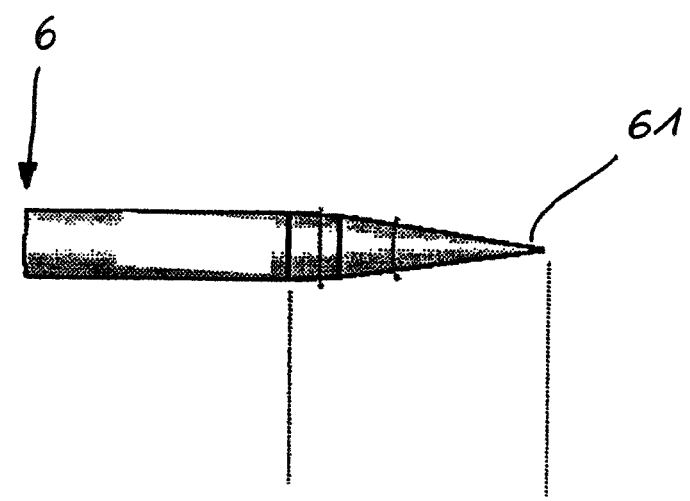
Fig. 10.1

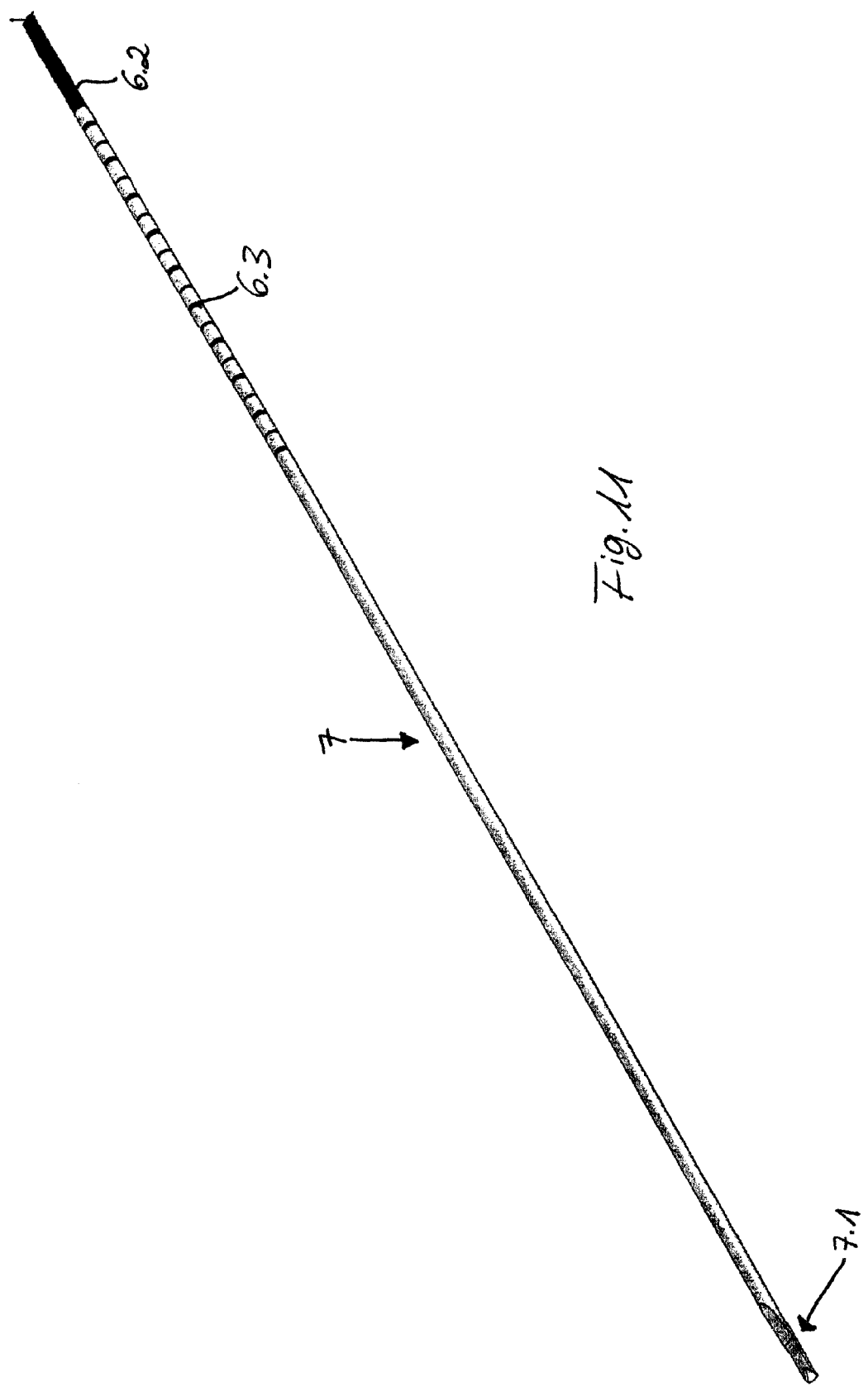

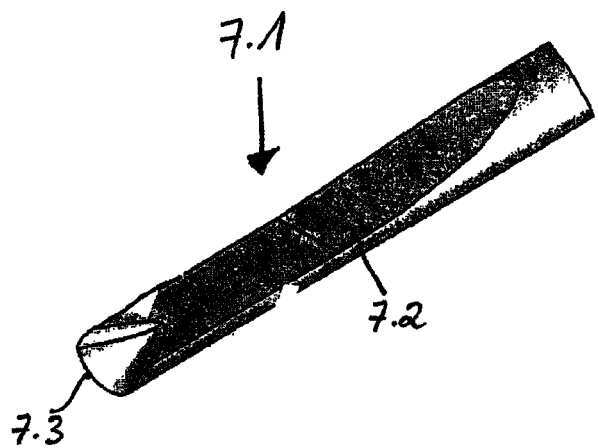
Fig. 11.1
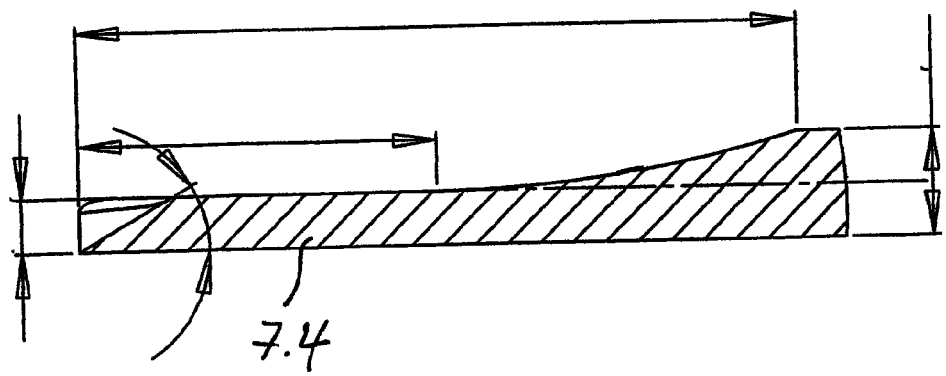
Fig. 11.2

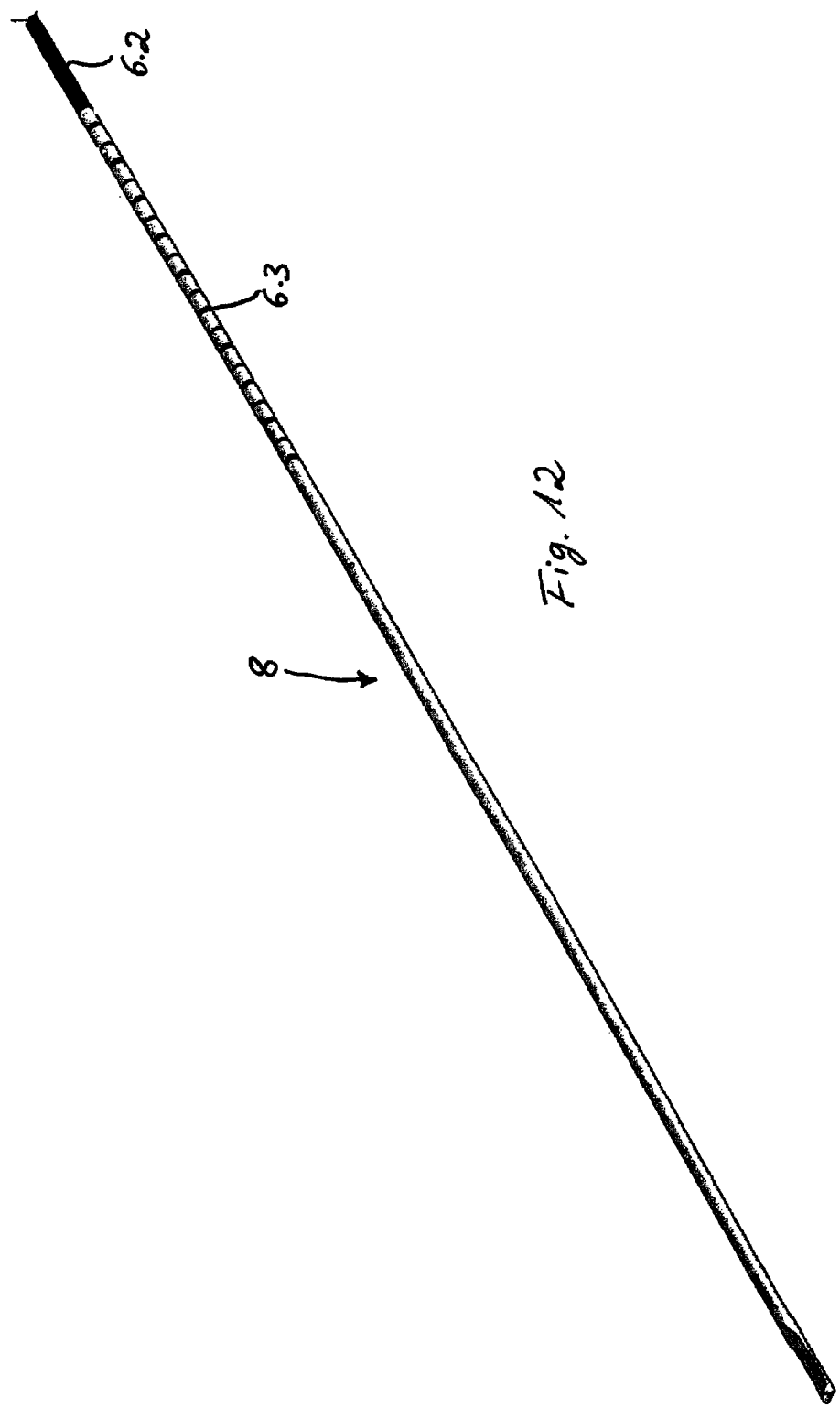

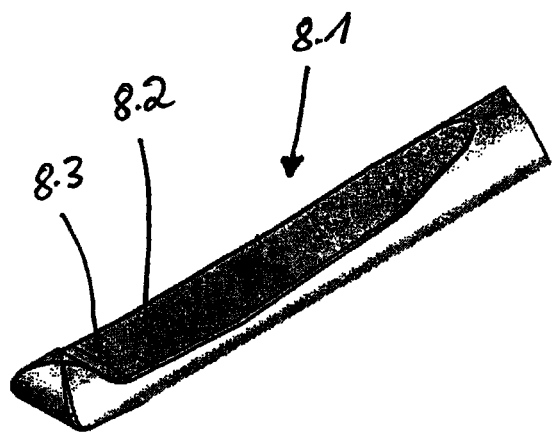
Fig. 12.1
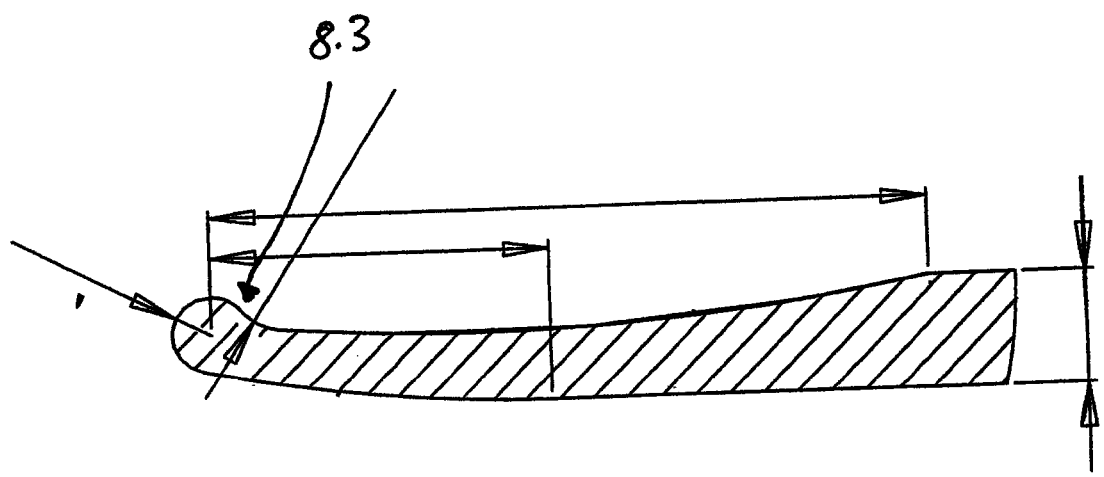
Fig. 12.2

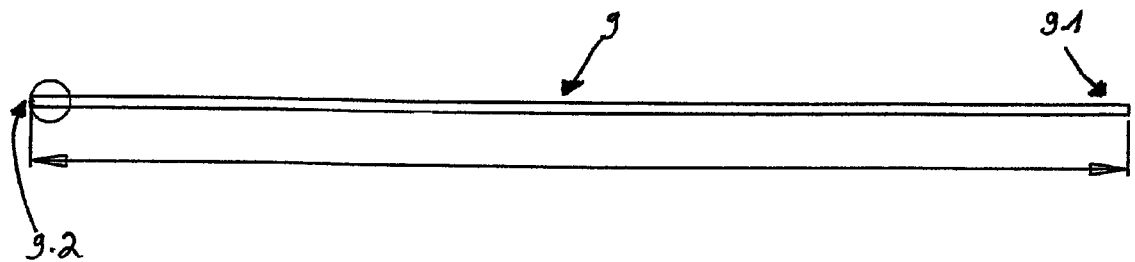
Fig. 13
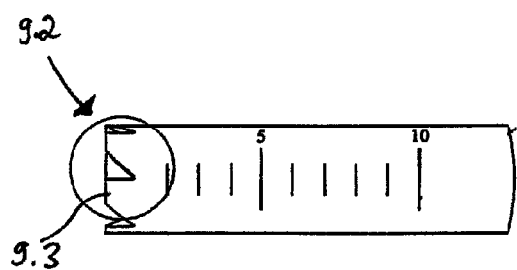
Fig. 13.1
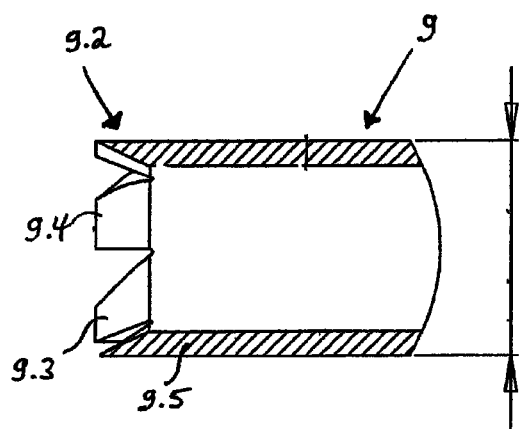
Fig. 13.2

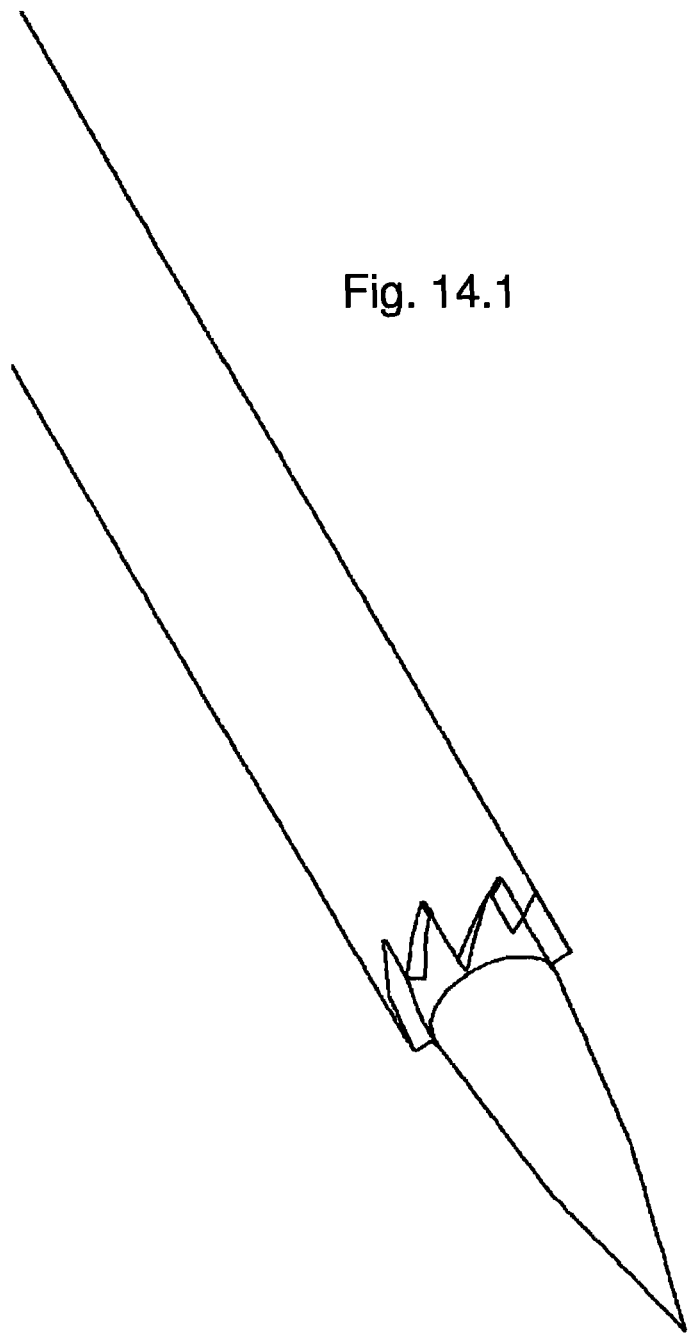
Fig. 14.1

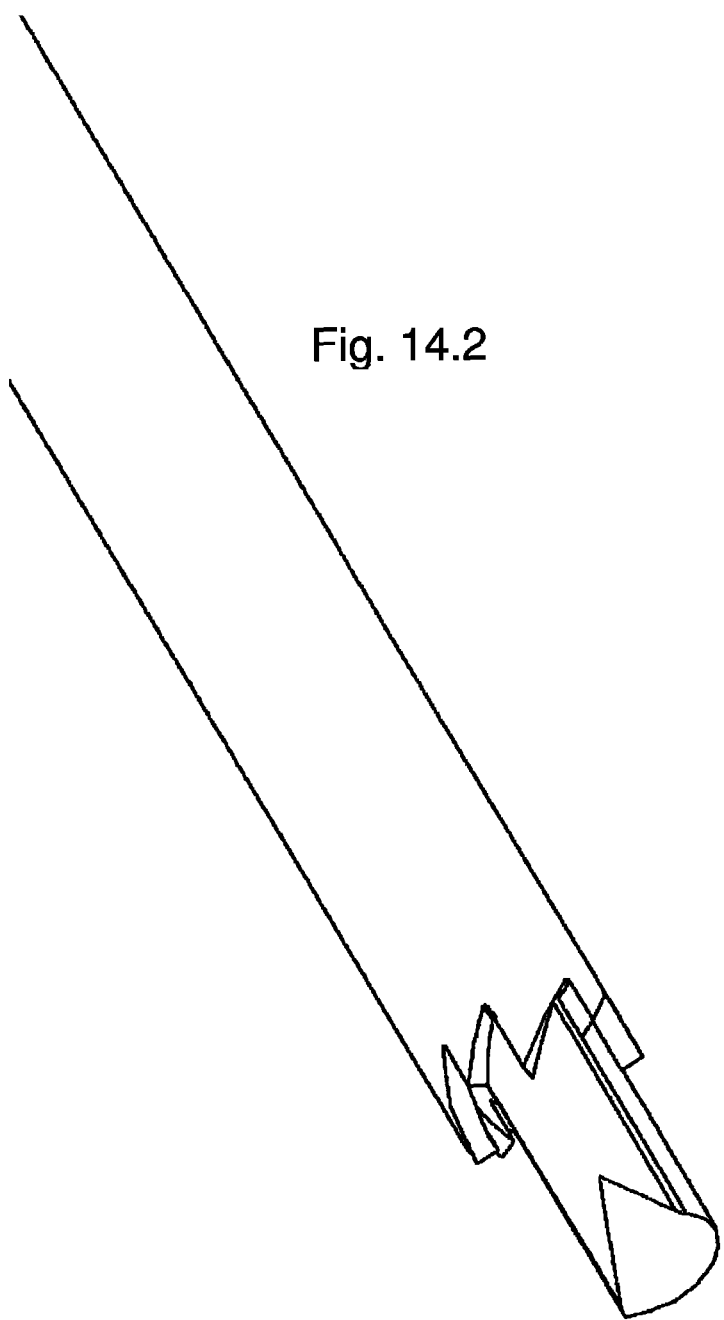
Fig. 14.2

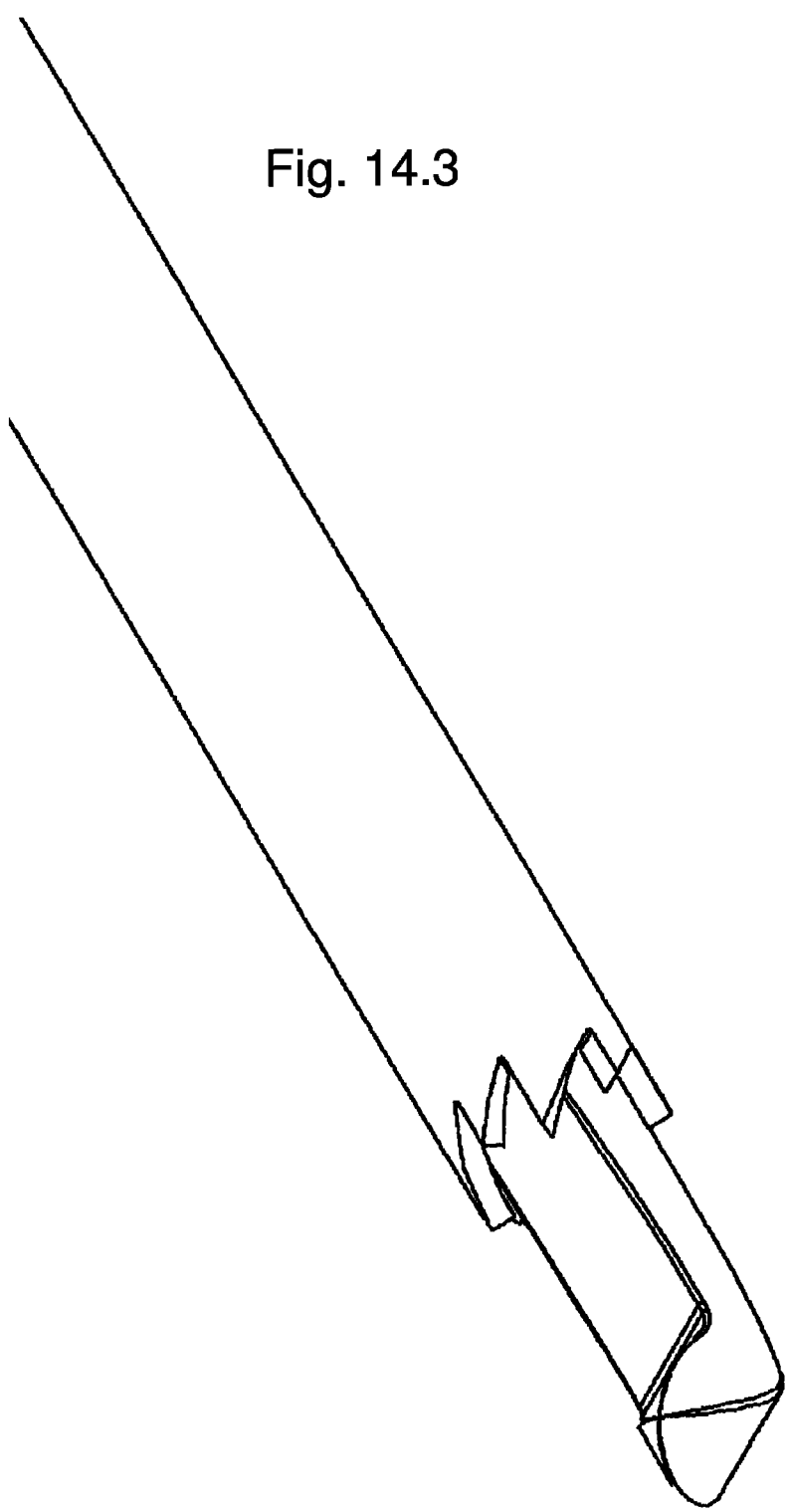
Fig. 14.3

DEVICE AND METHOD FOR MINIMALLY INVASIVE SPINAL INTERVENTION

CROSS REFERENCE TO RELATED APPLICATIONS

This application is a United States National Phase application of International Application PCT/EP2007/010238 and claims the benefit of priority under 35 U.S.C. §119 of Spanish Patent Application ES 2006 03026/4 filed Nov. 27, 2006, the entire contents of which are incorporated herein by reference.

FIELD OF THE INVENTION

The invention relates to a device for minimally invasive endoscopic intervention in the skeletal region, in particular on the spinal column, having the following elements: a cannula with a distal end having a generally bevelled shape relative to a symmetrical axis of the cutting tool, an optical probe (endoscope) for insertion through the cavity of the cannula; and to a method for minimally invasive intervention in the spinal region, having at least the following steps: at least one rod is brought percutaneously with its distal end at least as far as into the region of the intervention and a hollow tube with bevelled distal end is introduced at least as far as into the region of the intervention, through which hollow tube an endoscope is introduced.

The invention relates in particular to a device for removing tissue during endoscopic interventions, above all for removing bone tissue or connective tissue and other types of tissue.

The invention covers in particular the treatment of spinal stenoses, but also the preparative widening of access channels in relation to endoscopic intervention for treating prolapsed intervertebral discs, the invention not being limited to these possible applications.

BACKGROUND OF THE INVENTION

Various endoscopic techniques and devices are known for treating a prolapsed intervertebral disc in the spine. Basically, for example, after an incision has been made in the skin of the patient, first of all an elongate element with a tapered rounded tip is inserted (percutaneously), the purpose of which is adaptation of the soft tissue as far as into the immediate vicinity of the damaged disc requiring repair. Once this first elongate element has been introduced, a fine cannula is introduced thereover, the internal diameter of which matches the external diameter of the first elongate element. The external diameter of the cannula may be between 2 mm and 10 mm, with cannulae being used most frequently which have a diameter of approximately 6 mm. This cannula comprises a round cross-section and may have different shapes at its distal end, the distal end generally being bevelled in shape relative to the axis of the cannula, to allow a better view of the working area. After introduction of the cannula the first elongate element is removed, leaving an open access channel to the damaged disc, an optical probe (endoscope) being introduced, which is conformed to this channel and which in turn has channels for pressurized water for cleaning purposes and for sucking out material and working channels for working instruments, such as forceps or the like, for treating and working on the (disc) tissue.

However, the problem may arise that bone tissue or bony growths are present in the working area which hinder the cannula from advancing as far as into the region of the disc to be treated or which have a troublesome effect on the orientation of the cannula with regard to the working area. Often it is necessary, therefore, to use a cutting tool to cut or file away bone tissue so as to obtain access to the site needing treatment.

The techniques which are currently known offer two different solutions to this problem. The first one involves a cutting tool of a size which allows it to be introduced through a working channel of the optical probe. This solution allows the user to remove bone tissue while maintaining visual observation of his actions. However, the problem arises here that the tool has necessarily to have a very reduced diameter (maximum diameter 3.5 mm) and the process of removing bone tissue may take too much time, which is disadvantageous to the patient. The second known solution involves removal of the optical probe and use of a cutting tool with a larger diameter. The difficulty here is that the user has to undertake the intervention without a direct view of the soft tissue present, with the attendant risk of injury to nerve tissue in spiral regions.

In both cases the cutting tool is normally a cylinder, whose distal end is perpendicular to the axis of the cylinder. This distal end normally has a cutting edge of serrated construction. In particular, the diameter of the tool is different for each of the two stated solutions.

The object of the present invention is to propose a device and a method which, while avoiding the above-stated disadvantages, make possible in particular the effective removal of bone tissue in the case of spinal endoscopic intervention and allow visual observation of the intervention at any time by the user.

SUMMARY OF THE INVENTION

According to the invention, the stated object is achieved with a device of the above-mentioned type which is characterized in that that the cannula takes the form of a hollow cutting tool, in which the most distal region of the distal end comprises a cutting edge, which is incorporated into the edge of the wall of the cutting tool.

Furthermore, to achieve the stated object the invention provides the development of a method of the above type, in that the hollow tube constructed as a cutting instrument with a cutting edge at its front (most distal) end is moved at least percussively against a bone area to be removed.

In a preferred configuration of the device according to the invention, an outer hollow cannula is provided for receiving the cutting tool.

The cutting tool of the device according to the invention may be moved manually (movement of the cutting edge directly by the user's hand), automatically or by a combination of the two ways of proceeding. In the latter two cases, the device has an automatic drive means, so as to allow the cannula-type cutting tool provided with the cutting edge to effect a repeating vibratory movement. The drive may be arranged in a handle, the cutting tool or the corresponding cannula being connected to the drive's output shaft, which moves relative to the handle. Such a vibratory movement may be a to-and-fro movement in the longitudinal direction of the cutting tool and/or a to-and-fro swiveling movement about the axis of the cutting tool, preferably over up to a total of 30°, most preferably less than 12°, i.e. accordingly over 15° or up to 6° relative to a central neutral position. The vibrations contribute to reliable, easy cutting of the bone. The means for generating the movements may be of known type, and may include motors, electromagnetic mechanisms etc.

As is clear from the above, the invention also covers a cutting tool for removing tissue during endoscopic interventions, which may in particular be used as the cutting tool of the overall device according to the invention. The tool includes an element in the form of a hollow cannula, at the distal end of which there is located a cutting edge and which is distinguished in that the opening of the stated distal end is bevelled in shape relative to a symmetrical axis of the cannula-type element. Because the above-mentioned cutting edge is located at the most remote distal region on the end face of the wall of the cannula-type element, the inner cavity thereof is free, for receiving an optical probe.

So that the cutting tool does not injure any tissue upon introduction, it should preferably comprise a cut profile with a tapered surface, which joins the blade to the outside of the wall of the cannula. Preferably, the blade should be located at least at a radial distance from the inside of the cannula wall which amounts to only a quarter of the radial distance from the outside. It is preferable for the cutting edge to coincide or be aligned with the distal end of the inner side of the cannula wall. In a preferred configuration, the cutting edge is of serrated construction.

Due to the shape of the cutting edge, the cutting tool may be inserted into the human body in a similar manner to already known cannulae, without cutting injuries being caused to the tissue in the area of insertion. In addition, the stated tapered shape allows a correct view of the area to be cut from the inside out by means of an endoscope.

While the above-described tool with bevelled distal end and a cutting edge only at the area projecting furthest is used in particular to sever bony growths in the area where the tools are inserted towards the spinal canal, the invention provides a milling chisel which may be inserted through the endoscope for working on more medial narrowed portions, which milling chisel is in particular of hollow-cylindrical construction and comprises a circular-symmetrical set of teeth at its end-face end.

So that, when working with such a milling tool, guidance of the same is provided and thus the risk of damage to tissue which should not be damaged or indeed to nerves is reduced or eliminated, the invention provides in an extremely preferred development a device which comprises at least one anchoring tool which may be inserted through the endoscope, the device possibly also comprising, as a work kit, two or more such anchoring tools which may optionally be used as alternatives. The anchoring tools are constructed at their distal end in such a way that they may be fixed in particular to the posterior longitudinal ligament of the spinal column. For handling purposes, the anchoring tool is provided at its rear (proximal) end with a connection configuration for non-rotating connection with a handle or the like, the anchoring tool in particular being provided in its rear area, distally relative to the connection configuration, with graduations, in particular in the form of notches extending around part of the circumference of the connecting tool perpendicularly to the longitudinal axis thereof.

In a first preferred configuration, the anchoring tool is an endoawl, the endoawl comprising a sharp distal tip. In another configuration the anchoring tool is an endospatula, the endospatula being provided at its distal end with an end-face cutting edge. Finally, an extremely preferred configuration of the invention is characterized in that the anchoring tool is an endoelevator, the endoelevator in particular comprising in its distal end region firstly a taper and then a thickened portion at its outermost distal end.

The method according to the invention provides, in a preferred development, for the cutting tool to be swivelled over a limited angular range, the cutting tool alternatively or additionally being capable of being moved axially in cycles, i.e. percussively. A preferred further development provides, with regard to the swivel range, that the cutting tool is swivelled over an angular range of up to 30°, preferably of less than 12°. In a further development the method according to the invention provides, for the purposes of the above explanations relating to the removal of more medial stenoses, that an anchoring tool is inserted through the working cavity of an endoscope introduced as far as into the spinal column region and is anchored in the region of the posterior longitudinal ligament, with either an endoawl being introduced as the anchoring tool, which is percussively anchored axially with its sharp tip in the area at the posterior longitudinal ligament or adjacent areas of bone, or an endospatula with flattened distal end being introduced as the working tool and being anchored between the posterior longitudinal ligament and bone by axial application of force or indeed an endoelevator with a thickened portion at the distal end provided with an undercut being introduced as the working tool and being anchored between bone and posterior longitudinal ligament against the latter under tension.

To actually work on the more medial stenosis, a milling chisel is additionally introduced according to the invention over the working tool, acting as a guide tool, and the bone material to be removed is removed therewith by at least one swiveling movement of the milling chisel, the milling chisel likewise being capable of being rotated and/or moved axially in cycles. Drive is preferably achieved by means of a motor.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a schematic representation of a damaged disc (prolapsed intervertebral disc), which exerts pressure on nerve elements, together with an elongate element with round, tapered tip and a cutting tool according to the invention in the vicinity of the region to be operated on;

FIG. 3.1 shows an enlarged vertical section through the distal end region of a cutting tool according to the invention;

FIG. 3.2 is a side view, perpendicular to the axis, of the distal end region of a cutting tool according to the invention;

FIG. 3.3 is an enlarged perspective representation of the distal end region of the cutting tool according to the invention;

FIG. 3.4 is a side view of the distal end region of another embodiment of the cutting tool according to the invention;

FIG. 5.1 shows a longitudinal section through the distal end of a cutting tool according to the invention with modified cutting region;

FIG. 5.2 is a plan view of the distal end of the modified cutting tool according to the invention as in FIG. 5.1;

FIG. 10 is a perspective side view of an endoawl as a guide element for a milling chisel;

FIG. 10.1 is an enlarged representation of the distal tip of the endoawl of FIG. 10;

FIG. 11 is a perspective representation of an endospatula sharpened at the distal end as a guide for a milling chisel;

FIG. 11.1 shows an enlarged distal end of the endospatula of FIG. 11;

FIG. 11.2 shows a longitudinal section through the distal end of an endospatula;

FIG. 12 is a perspective representation of an endoelevator with blunted distal end as a guide for a milling chisel;

FIG. 12.1 is an enlarged representation of the distal end of the endoelevator of FIG. 12;

FIG. 12.2 is an enlarged longitudinal section through the distal end of the endoelevator;

FIG. 13 is a side view of a milling chisel with hollow shank;

FIG. 13.1 is an enlarged side view of the distal end of the milling chisel of FIG. 13;

FIG. 13.2 shows an enlarged longitudinal section through the distal end of the milling chisel of FIG. 13;

FIGS. 14.1-14.3 are representations showing the interaction of endoawl, endospatula and endoelevator with a milling chisel of FIG. 13.

DESCRIPTION OF THE PREFERRED EMBODIMENTS

Figure 1:
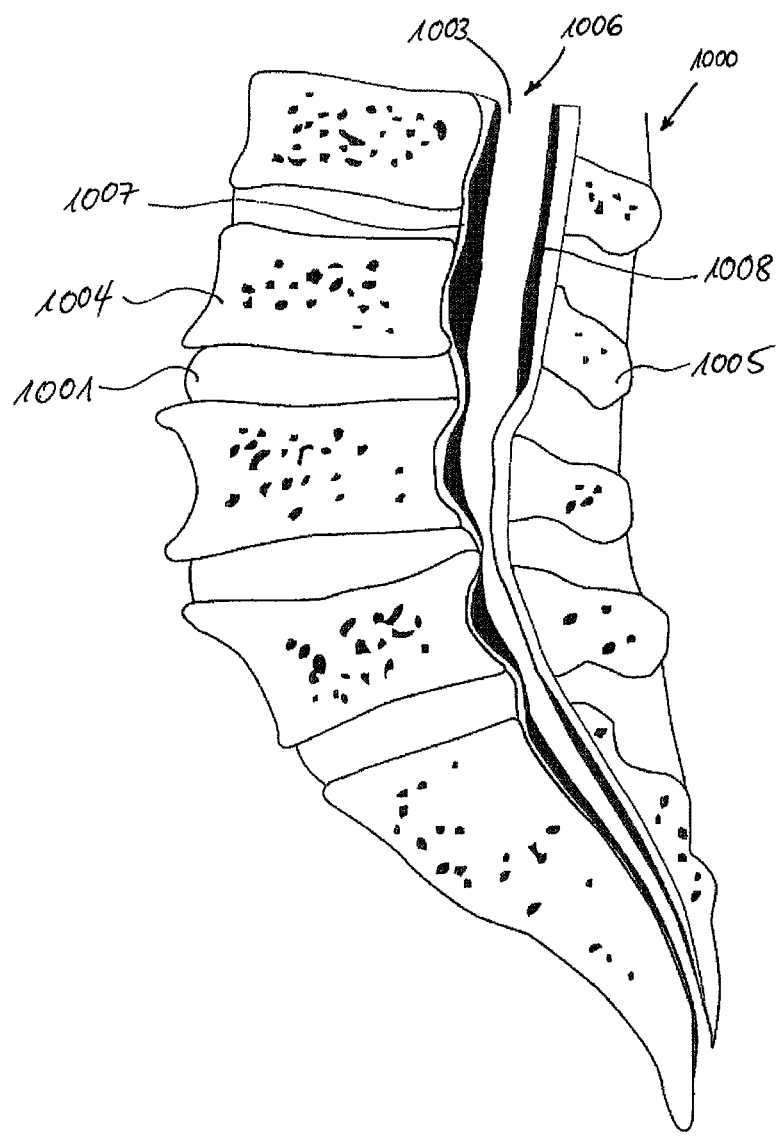
FIG. 1 shows the lower part of a spine to illustrate the corresponding physical conditions.

Referring to the drawings in particular, FIG. 1 shows in longitudinal section the lower area of a spinal column 1000 with vertebrae 1004 and the spinous process (Processus spinosus) 1005 extending backwards (dorsally) away therefrom, between which—in the cross-section shown—are located the vertebral holes (vertebral foramen) forming the spinal canal 1006 of the spinal column 1000. Between the vertebrae 1004 there are located the intervertebral discs 1001 with their nucleus 1002 (FIG. 2) and their ring (annulus) 1001a.

The vertebrae are connected together at the front (ventral) side of the spinal canal by the anterior longitudinal ligament 1007 (Ligamentum longitudinale anterius), while the posterior longitudinal ligament (Ligamentum longitudinale posterius) 1008 is located to the rear of the spinal canal 1006, in front of the spinous processes 1005, the posterior longitudinal ligament being connected only loosely to the vertebrae but firmly to the discs 1001. Nerve tissue 1003 extends through the spinal canal 1006, individual nerves 1009 (FIG. 2) exiting laterally between the vertebrae 1004. To the side of the spinal canal 1006 (concealed by the nerve tissue 1003 and therefore not visible in FIG. 1) there is in each case located a "yellow" ligament (Ligamentum flavum) which is located in each case between two vertebrae and stabilizes the spinal column.

Figure 2:
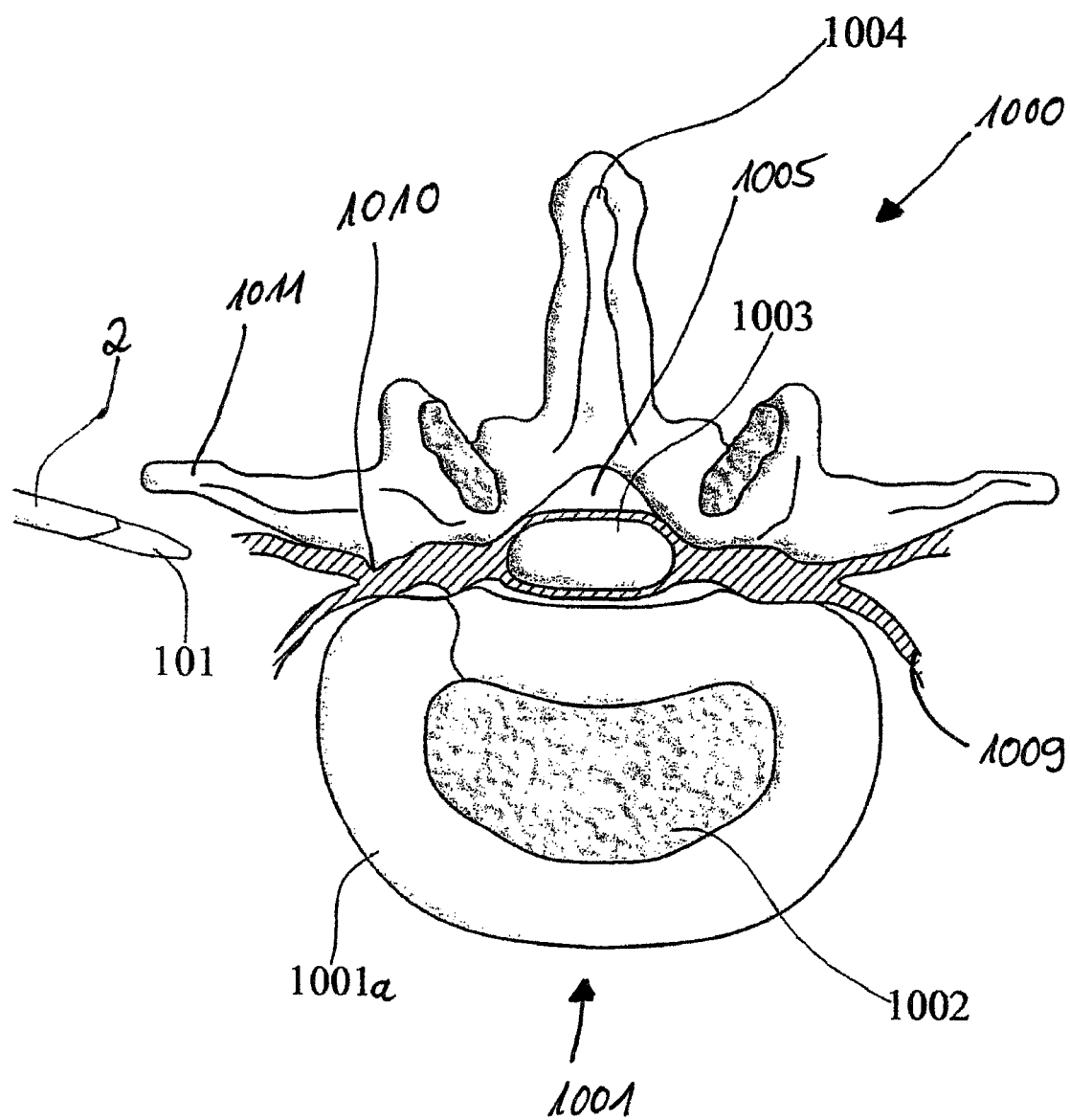

As is visible in particular from FIG. 2, there is a possibility in particular of minimally invasive access to the spinal canal 1005 at the level of the discs 1001, for example to remedy prolapsed discs, which press on the nerve tissue 1003 in the spinal canal 1005 and cause pain.

A bony growth 1010 on a transverse process (Processus transversus) 1011 of the vertebra 1004 towards the vertebral body or the disc is visible, which narrows access to the medial region of the spinal canal 1005 and prevents a hollow tube of sufficiently large diameter for introduction of an endoscope from being inserted.

The cutting tool 2 according to the invention is constructed at its distal end for removal of the bony growth 1010.

To this end, hitherto an elongate guide element was initially introduced, over which, optionally in the context of a dilatation process, one or more cannulae, in particular a cannula with a distal end and with generally tapered geometry relative to the axis of symmetry, were introduced, so preventing in particular the entraining of tissue located in the operation region to the region treated. The distal end may for example be flat in shape, but other shapes are also possible and known, provided that the end is more distal at a first part than at a second part, i.e. has a generally oblique shape with regard to the axis of symmetry of the cannula.

The edges, which are defined by the wall of the cannula, are rounded, in order to counteract the risk of injury to tissue during introduction of the cannula.

Working instruments or an optical probe or an endoscope are introduced through the hollow region of the cannula. In the latter case, this is so as to be able to obtain images of the working area. In addition, inlet and outlet channels may be provided in the cannula for rinsing through with pressurized water. This pressurized water is used to remove residues and to obtain a cleaner camera image of the operation region. An endoscope is an apparatus with a substantially cylindrical main body with an optical channel, which optionally comprises a light guide and through which light may exit from the distal end of the apparatus to illuminate the surrounding area and from there an image may enter, which may be observed directly at the proximal end by way of a microscope or indirectly using an image converter and a screen. In the present case of minimally invasive operative intervention, the elongate main body of the endoscope in any case additionally comprises a hollow working channel, through which working instruments may be guided and introduced from the proximal end to the distal end.

FIG. 2 shows introduction of a cutting tool according to the invention or a cutting cannula, as will be described in greater detail below, over an elongate guide element 101 from the side towards the spinal canal 1006. The elongate element 101 is introduced through an incision in the skin of the patient into his/her body. The tapered round tip serves to push endogenous tissue to the side, so as to allow the introduction of a cannula for the endoscope, without that this causing damage within the body. The cannula has an internal diameter which corresponds roughly to the external diameter of the elongate element 101. In this way, tissue is prevented from being pushed into an otherwise possible gap between the elongate element 101 and the cannula and severed. Once the cannula has been introduced, the elongate element 1001 is removed, such that the inside of the cannula is hollow. The inside of the cannula is used by the user as a working area and cutting instruments, optical probes (endoscopes), forceps etc. may be introduced. Moreover, working channels may be present inside the probe, in order to create a flow of pressurized aqueous liquid, which serves to keep the endoscope clean, such that it is possible to see the operation region, and may be used to remove residues arising during the intervention. All instruments which are introduced into the cannula are elongate in shape. Thus, for instance, the hitherto known cutting instruments have an elongate cylindrical shape with an oblique, saw blade-shaped end, which simplifies cutting.

The diameter of the cannula is limited for obvious reasons (restriction of tissue expansion and of the incision to be performed). As a consequence of this limitation, the inside of the cannula merely allows the simultaneous introduction of an optical probe with an additional working channel for a cutting tool of very reduced diameter, which may not be very useful in meeting the requirements of cutting bone tissue. In these cases it is necessary to remove the optical probe from the inside of the cannula and to introduce a non-optical probe, which has a wider working channel for a larger diameter cutting tool. In this case, cutting of bone tissue proceeds blind, i.e. without the possibility of observing the soft tissue, which is clearly very dangerous, since nerve tissue can be irreparably damaged and the success of the intervention depends on the dexterity of the operating surgeon.

To avoid these difficulties, the cannula according to the invention takes the form of a cannula-type cutting tool 2. This has a distal end 22 bevelled relative to the axis of symmetry 25 of the cannula. The size of the cutting tool 2 allows introduction into the body in the above-described manner and simultaneously allows positioning of an optical probe through the inside thereof, in a similar manner to already known cannulae.

The characteristic feature of the present invention is that the cutting tool 2, which constitutes the core subject matter of the invention, has a cutting edge 26 at the most distal region of the distal end, i.e. at the end-face edge of the cannula wall 21.

Figure 4:
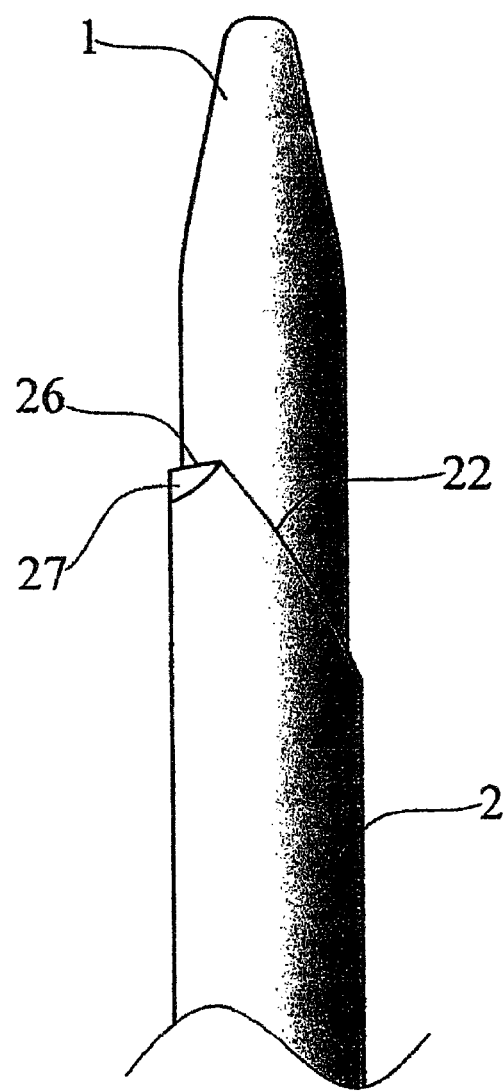
FIG. 4 is a side view of a cutting tool according to the invention with an elongate element with rounded, tapered tip (a probe) inside the cutting tool.

The fact that the cutting edge 26 is located at the endface edge of the cannula wall results in the cutting tool 2, which constitutes the subject matter of the invention, being able, like a cannula of the endoscopic systems of known type, to be introduced into the body. Then when an elongate element 101 is introduced, which fills the entire inside, the cutting edge 26 cannot sever the tissue, as is clear from FIG. 4. On the other hand, the general oblique shape of the distal end of the cutting tool 2 allows a correct view of the region to be cut from the inside of the cannula-type cutting tool 2 out.

In the case of the example shown in FIG. 3, the cutting edge 26 lies on the inner side of the cannula wall 21. Moreover, the cutting edge 26 consists of a cut 27 in the cannula wall 21, which extends obliquely relative to the outside of the wall towards the inside in the region of the distal end 22 of the tool 2 (FIG. 3, 4).

FIG. 3.3 shows that a graduation 23 or scale is located on the inside of the extension of the cutting tool 2, for example by means of etched-in transverse indentations. In addition, the edge of the end-face opening of the cutting tool 2 is rounded apart from in the area of the sharp edge 26 located at the front end face. Finally it is apparent from FIG. 2 that in the embodiment illustrated herein the end face of the cutting tool 2 is not merely bevelled but rather in side view is initially arcuate from the proximal side of the opening and only flattens out obliquely in its distal end region, wherein it here preferably forms an angle of the order of 10 to 20° with the longitudinal axis or side wall. The diameter of a cannula-type cutting tool 2 according to the invention should be greater than 3 mm and preferably lie in the range from 5 to 7 mm.

FIG. 5 shows an alternative configuration of the cutting tool 2, which constitutes the subject matter of this invention. In this case the cutting edge 26 is serrated and does not coincide with the inside of the cannula wall 21. However, this tool does not cause cutting injuries to tissue either, if it is introduced in the ways described above.

Figure 6:
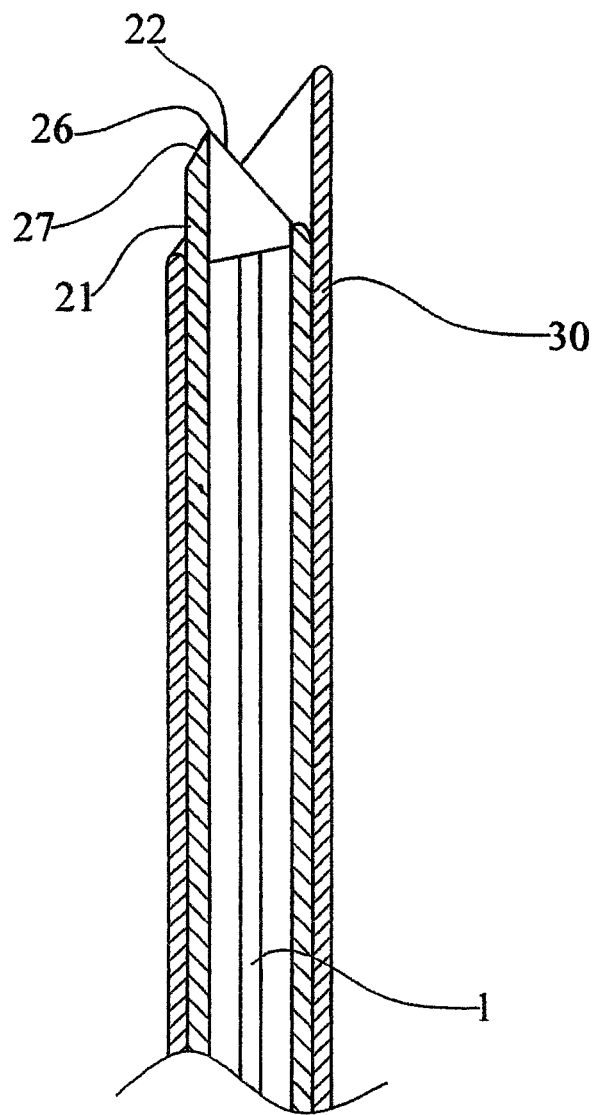
FIG. 6 is a schematic representation of a device according to the invention with a cutting tool according to the invention in longitudinal section.
Figure 8:
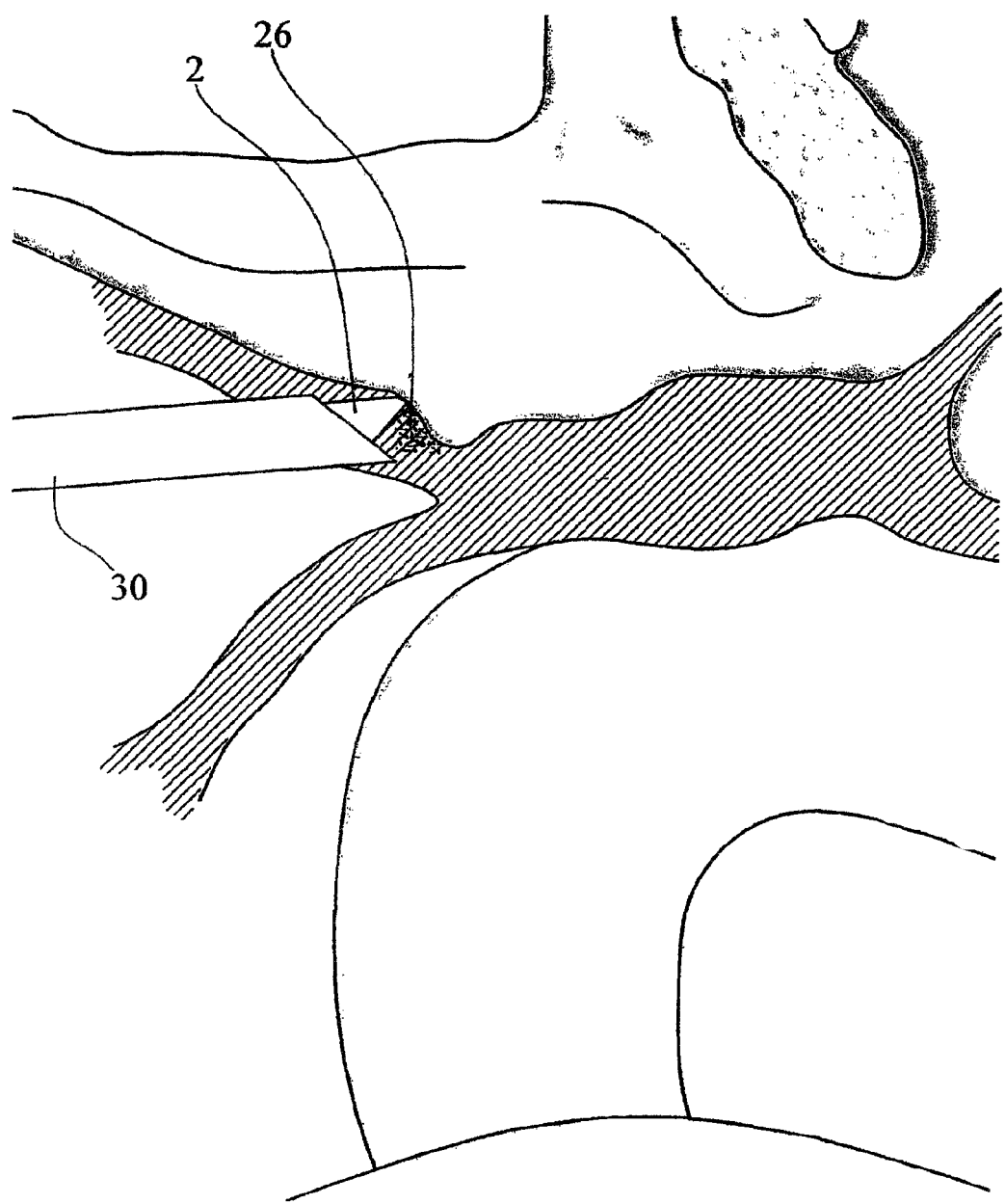
FIGS. 8 & 9 show schematic representations of the device according to the invention ready for use.
Figure 9:
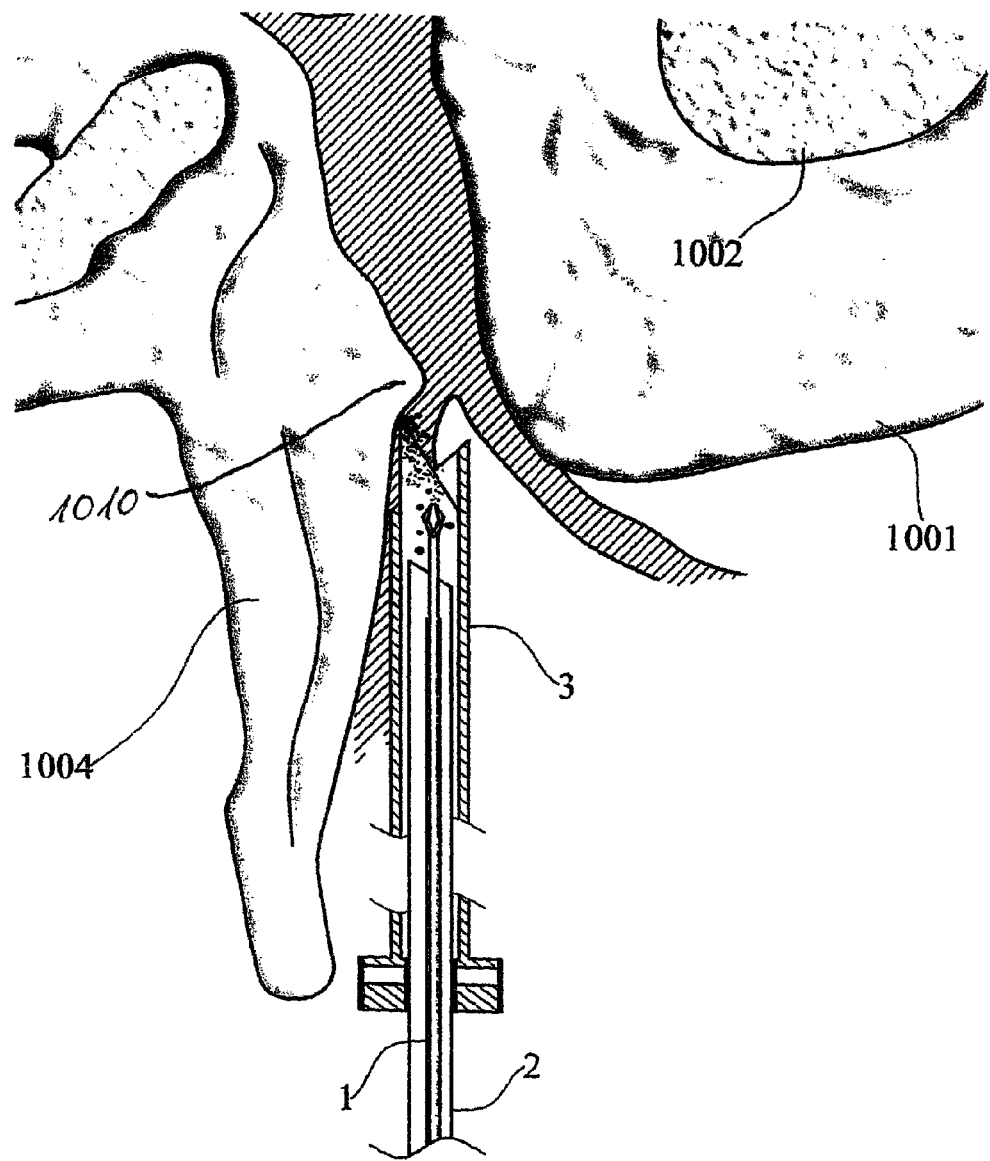

In the examples illustrated in FIGS. 3.1, 3.2 and 5.1, 5.2 the opening of the distal end of the cutting tool 2 is defined by a plane. However, this opening may also assume other forms, such as for example a curved surface (FIG. 3.3) etc. The cutting tools 2 may have a similar diameter to that of the outer cannulae of the prior art devices, but in particular and advantageously have a somewhat larger diameter, such that endoscopes with larger diameters than hitherto may also be used. In the case of a system according to the present invention, the cutting tool 2 combines the functions of the outer cannula and of the cutting tool. The system according to this invention is completed by an optical probe 1 (endoscope), which is located inside the cannula-type cutting tool 2 with the cutting edge 26 and has a working channel for tools. It is advantageous to use a further, outer, hollow cannula 30 with a diameter which is greater than or equal to that of the cutting tool 2 with cutting edge 26. This external cannula 30 may be conformed to the cutting tool 2 with cutting edge 26 and correspond with regard to its configuration to known outer cannulae (not in its diameter). By way of this cannula 30 better monitoring over the working area is achieved, e.g. through the pouring in of pressurized fluid through a working channel FIG. 6 shows a device of this type. FIGS. 8 and 9 show schematic representations of the mode of operation. The outer cannula 30 is immobile, while the cutting tool 2 moves in order to cut the bony growth 1010. Under these conditions, pressurized fluid may for example be rinsed through the working channel, such that the dimensions of the working space through which the pressurized fluid is rinsed do not vary with the movement of the cutting tool 2.

Figure 7:
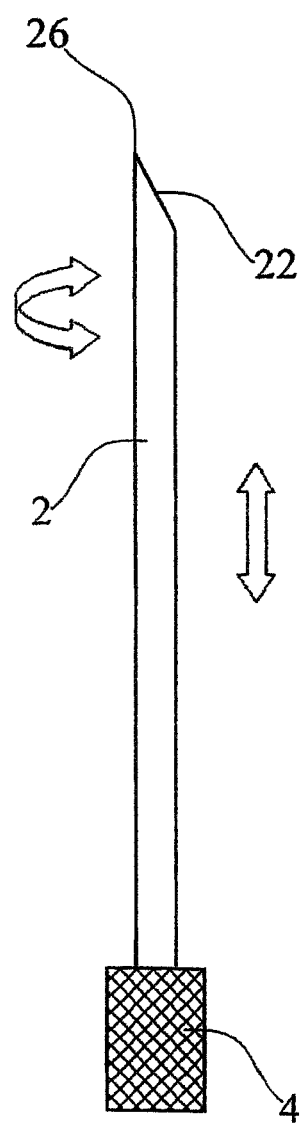
FIG. 7 is a side view of a further configuration of a device according to the invention.

The invention thus also has the advantage of being able to cut without impairing the working channels of the optical probe. In FIG. 9 endoscopic forceps are inserted through a working channel of the probe 1. Moreover, as is clear from FIGS. 7 to 9, the system may have means 4 for allowing alternating movement of the cutting tool 2, so as in this way to simplify cutting of the bone tissue. Various techniques are available for allowing this type of movement: pneumatic, magnetic, electrical, mechanical systems etc. Therefore, they will not be described in any further detail here. These means may include means of allowing movement lengthways relative to an axis of the cutting tool 2 or an alternating movement about an axis 25 of the tool, preferably with the swiveling movement being restricted to a radius of up to 15°, in particular less than 6° with regard to a neutral position, thus with a total swivel range of 30° or preferably up to 12°.

As far as size is concerned, the cutting tool 2 may have an internal diameter of between 2.7 mm and 7.3 mm, but preferably between 3.2 and 6.1 mm. The length of the cutting tool and the further means may correspond to those of the already known systems.

The method according to the invention thus so far comprises the following:

In the case of a skin incision, first of all at least one rod-shaped tool is introduced. Preferably, a plurality of tubular dilating tools of increasing diameter are introduced one over the other, until finally the cutting tool according to the invention may be introduced. The dilating rods fitting closely inside the same are removed and then an endoscope is introduced through the cutting tool as far as the distal region of the cutting tool, such that the working area of the cutting edge of the cutting tool may be monitored.

Then work with the cutting tool may proceed by rhythmic or cyclic percussion and swiveling to-and-fro, in order to remove a bony growth, a bony protrusion or the like.

In particular, if the restriction actually caused by bone marrow is situated in the entry zone of the introduction channel, as is the case with the narrowed portion 1010 of FIG. 1, "freehand working", as described above, is possible. However, this is less or no longer applicable where bone material to be removed is more medial and closer to nerve tissue 1003, since slippage of the sharp edge 26 of the cutting tool 2 may lead to nerve damage. In this case, at least a degree of reliable guidance is needed for cannula-type working tools. It is therefore necessary to anchor guide tools for cannula-type working tools reliably with their distal end in the spinal canal or in material defining the latter.

To this end, the invention firstly provides, in a first configuration according to the invention, an endoawl 6, as illustrated in FIG. 10. The endoawl 6 in FIG. 10 comprises a solid elongate rod with a pointed, sharp distal end 6.1, a rear or proximal non-circular-symmetrical gripping end 6.2, on which a handle may be non-rotatably mounted, and a graduation 6.3 likewise arranged in the rear or proximal area produced by lines in the form of indentations arranged at the circumference perpendicularly to the longitudinal axis.

The endoawl 6 has a total length of between 300 mm and 400 mm, preferably 370 mm, a gripping end 6.2 of between 20 mm and 30 mm, preferably 25 mm, a length from the last distal graduation line to the tip of between 200 mm and 300 mm, preferably 250 mm, and a tip length of between 5 mm and 15 mm, preferably 10 mm. The diameter of an endoawl 6 according to the invention is between 2 mm and 3.5 mm, preferably in the range from 2.6 mm to 3 mm. The conical tip 6.1 is subdivided into two portions with a shorter portion, which has a conicity of 6°, and a longer portion with a conicity of 17°, the latter extending over approximately three quarters to four fifths of the total length of the conical tip 6.1.

The endoawl 6 is anchored to internal material at the posterior longitudinal ligament by axially acting force, such as for example by means of hammers. The endoawl 6 may then serve to guide a milling chisel, as described further below.

Once the entry zone has been widened in the above-described manner, the endoawl 6 is introduced endoscopically with observation, i.e. through the working cavity of an endoscope, and anchored in place.

It is possible that in certain cases anchoring merely by driving in an endoawl 6 with a sharp tip is unsuitable or insufficient.

In this case the invention additionally or alternatively provides an endospatula 7 for anchoring purposes, as illustrated in FIGS. 11 and 11.1. The endospatula 7 also comprises a solid, rod-type elongate cylindrical body. It is provided with the same gripping end 6.2 and the same graduation 6.3 as the endoawl 6, for which reason the same reference numerals are also used. However, its distal end region 7.1 is configured markedly differently from the endoawl 6. As is clear in particular from FIG. 11.1, the distal end region firstly comprises an arcuate flattened portion 7.2, which then develops into a sharp end-face edge 7.3, similar to the edge of the cannula-type cutting tool 2, wherein this edge is located however on the outside 7.4 of the endospatula 7, as is apparent in particular from FIG. 11.2. The rounded flattened area, starting from the cylindrical main part of the endospatula 7, inclines not in a straight line, but rather in rounded manner with a radius of preferably 35 mm. This is adjoined as far as the distal end of the edge 7.3 of the endospatula 7 by a flat portion, which has approximately the thickness of half the diameter of the main portion of the endospatula 7, with a length of 7 mm to 15 mm, preferably 10 mm. The bevel to the distal sharp edge 7.3 proceeds at an angle of approximately 25° to 35°, preferably 30° to the longitudinal axis of the endospatula 7.

As a result of this configuration, it is possible, by means of the edge of the endospatula 7, preferably with observation, for example in between the posterior longitudinal ligament between the latter and the adjacent bone region, for the distal end of the endospatula 7 to be inserted and anchored there, in order in this way to achieve better, more reliable anchoring than is possible with the endoawl.

Finally, FIGS. 12, 12.1 and 12.2 show an "endoelevator" 8, whose distal end may engage behind the posterior longitudinal ligament. Here too, identical parts are again designated with identical reference numerals, i.e. the proximal gripping end 6.2 and the graduation 6.3. The endoelevator 8 is likewise constructed as a solid hollow shank with a diameter of the order stated above in relation to the endoawl. Its distal end region 8.1 is similar to that of the endospatula 7, being tapered and flattened down to roughly half the diameter of the solid shank, the taper proceeding by way of a rounded portion with a radius of 60 mm, which is firstly adjoined distally on the tapered side by a flat area 8.2, on the back of which there is provided convex rounding with a radius of the order of 40 mm about an axis perpendicular to the longitudinal axis of the endoelevator. When viewed in longitudinal section, the front end is thickened and partially circular, such that an undercut is produced at 8.3. This enables the endoelevator to grip behind the ligaments and also to obtain a certain hold thereon under tension.

As already stated, all of the endoawl, endospatula and endoelevator are fixed in the region of the posterior longitudinal ligaments, in order to serve as guides for a milling chisel, as illustrated in FIGS. 13, 13.1 and 13.2.

The milling chisel 9 comprises an extended hollow cylinder of a length which is somewhat less than the length of endoawl, endochisel, and endoelevator. The proximal end 9.1 (not explained here in any more detail) is provided with a coupling configuration, which allows non-rotatable, axially fixed coupling of a handle or rotary drive, like the coupling disclosed in DE 20 2005 016 761.4 U, to which reference is made and which is deemed to be part of the disclosure of the present application.

The distal end 9.2 is provided with teeth 9.3, the teeth tapering radially to a point, but over the circumference having a finite direction of extension, i.e. comprising a cutting edge 9.4. The front tooth flank is axially parallel, while the rear tooth flank forms an angle with the axis of the order of 40° to 50°, preferably 45°. The cutting edge 9.4 is located on the outer circumference of the shell 9.5 of the milling chisel 9.

In addition, on the outside of the shell 9.5 of the milling chisel 9 in the distal end region there is located a graduation, once again formed of indentations or notches extending perpendicularly to the axis in the circumferential direction, which, when the milling chisel 9 is inserted through the working cavity of an endoscope into the working area thereof, may be seen and observed by way of the lateral viewing optics at the distal end of the endoscope.

FIGS. 14.1 to 14.3 show the interaction of a hollow-cylindrical milling chisel 9 with an endoawl 6, an endospatula 7 or an endoelevator 8, which in each case extend through the cavity of the milling chisel.

Figure 15:
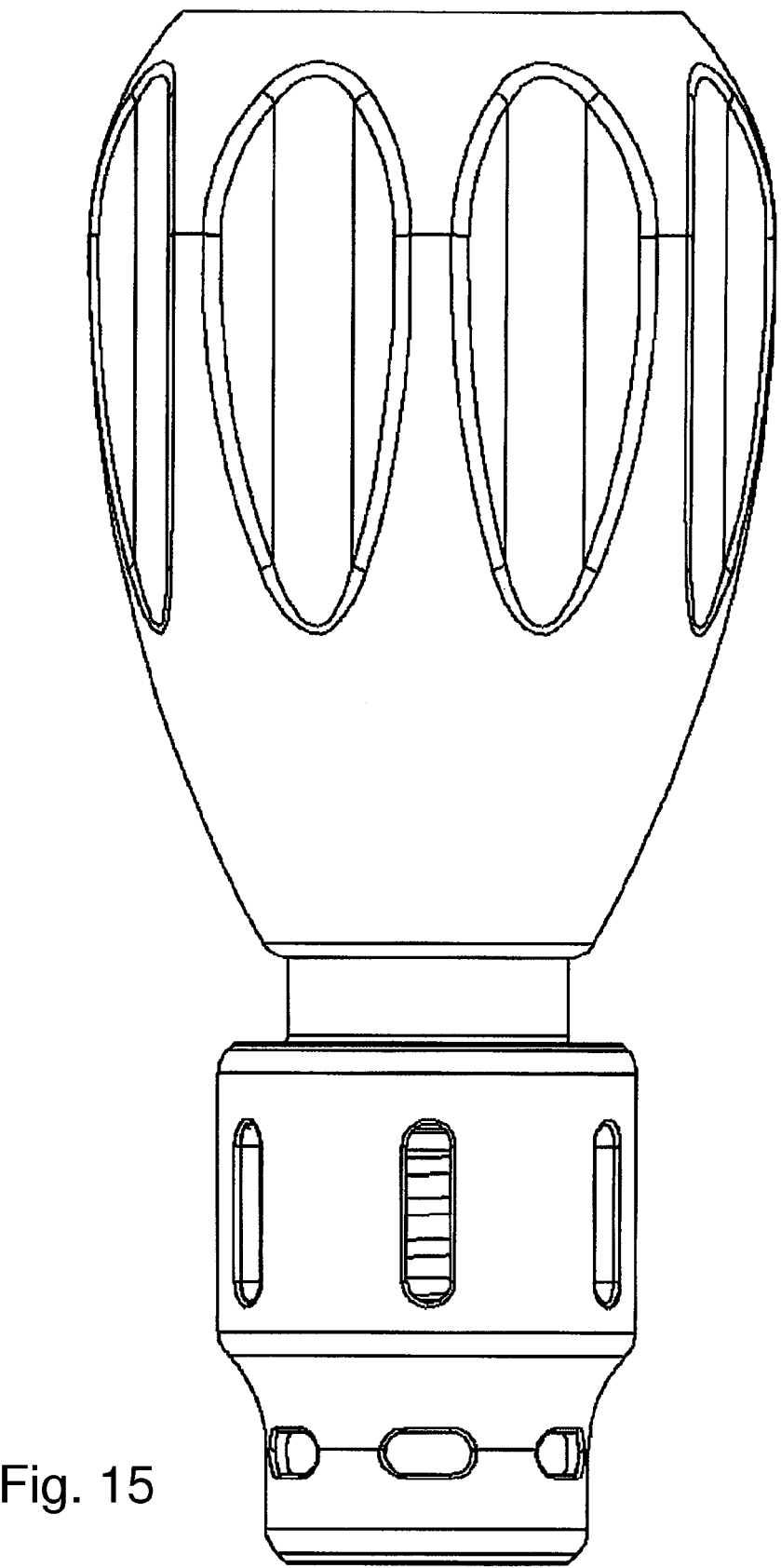
FIG. 15 is a side view of a handle for connection to the above-stated tools.

Finally, FIG. 15 is a schematic representation of a handle with a drive inside it and a coupling corresponding to DE 20 2005 016 761.4 U.

The further procedure using endoawl 6, endospatula 7 or endoelevator 8 and milling chisel 9, once the endoscope has been introduced in the above-described manner, is as follows:

One of the tools 6, 7 or 8 is advanced through the working channel of the endoscope extending through the cutting tool 2 as far as the longitudinal ligament at the level of the operation area and anchored there in the manner described, either by pushing in or squeezing between longitudinal ligament and bone material or by hooking behind the longitudinal ligament.

Then the milling chisel 9 is pushed through the working channel of the endoscope over the tool 6, 7 or 8 and, when it reaches its working or operation region, is set in rotation, such that material in the way of the teeth, such as bony growths or ligament cartilaginification, which press on nerves, may be removed. The internal diameter of the milling chisel 9 is here somewhat greater than the external diameter of the corresponding tool 6, 7 or 8, such that the milling chisel 9 is guided thereby but nevertheless slight lateral mobility is possible and therefore the operating surgeon is provided with a certain degree of working freedom.

While specific embodiments of the invention have been described in detail to illustrate the application of the principles of the invention, it will be understood that the invention may be embodied otherwise without departing from such principles.

The invention claimed is:

1. A device for endoscopic intervention in the skeletal region, in particular on the spinal column, the device comprising:
   a cutting tool comprising an element in the form of a hollow cannula, said hollow cannula comprising a cutting edge at a distal end thereof, wherein said distal end forms only one face defining an opening, said one face and said opening being generally bevelled in shape relative to a longitudinal axis of symmetry of the element, said cannula comprising a cavity, said opening extending over an entire cross section of said cavity, said cutting edge extending predominantly in a direction perpendicular to said longitudinal axis of said element;
   an optical probe (endoscope) moveably mounted in said cavity for insertion through the cavity of the cannula and out of said opening at said distal end;
   a means for moving the cutting tool relative to said optical probe, said means for moving the cutting tool brings about a cyclic movement in the longitudinal direction of the cutting tool.

2. A device according to claim 1, wherein the cutting edge is joined to the outside of the wall of the cutting tool via a tapered surface.

3. A device according to claim 1, wherein the radial distance between the cutting edge and the inside of the wall of the cutting tool amounts to at most a quarter of the distance between the cutting edge and the outer surface of the wall.

4. A device according to claim 3, wherein the cutting edge coincides with the end of the inside of the wall of the cutting tool.

5. A device according to claim 1, further comprising an outer hollow cannula for receiving the cutting tool.

6. A device according to claim 1, wherein the means for moving the cutting tool brings about a cyclic swiveling movement about a longitudinal axis of symmetry of the cutting tool.

7. A device according to claim 6, wherein the means for moving the cutting tool brings about a cyclic movement about a longitudinal axis of symmetry of the cutting tool over a swivel radius of in each case up to 15°, preferably less than in each case 6° with regard to a neutral position.

8. A device according to claim 1, wherein the cavity of the cutting tool has an internal diameter of between 2.7 mm and 7.3 mm.

9. A device according to claim 1, wherein the cutting edge is of serrated construction.

10. A device according to claim 1, further comprising a milling chisel which may be inserted through the endoscope.

11. A device according to claim 10, wherein the milling chisel is of hollow-cylindrical construction.

12. A device according to claim 1, further comprising at least one anchoring tool which may be inserted through the endoscope.

13. A device according to claim 12, wherein the anchoring tool may be fixed with its distal end to the posterior longitudinal spinal ligament.

14. A device according to claim 12, wherein the anchoring tool is provided at its rear (proximal) end with a connection configuration for non-rotatable connection with a handle or the like.

15. A device according to claim 12, wherein the anchoring tool is provided in its rear area distally of the connection configuration with graduations, in particular in the form of notches extending around part of the circumference of the connection tool perpendicularly to the longitudinal axis thereof.

16. A device according to claim 12, wherein the anchoring tool is an endoawl.

17. A device according to claim 16, wherein the endoawl comprises a sharp distal tip.

18. A device according to claim 12, wherein the anchoring tool is an endospatula.

19. A device according to claim 18, wherein the endospatula is provided at its distal end with an end-face cutting edge.

20. A device according to claim 12, wherein the anchoring tool is an endoelevator.

21. A device according to claim 20, wherein the endoelevator comprises in its distal end region firstly a taper and then a thickened portion at its outermost distal end.

22. A device according to claim 12, further comprising a handle connectable to the anchoring tool.

23. A device according to claim 10, further comprising a drive, preferably a rotary drive, in particular a rotary drive with chiselling action for the milling chisel.

24. A device according to claim 10, further comprising at least two of the following anchoring tools: endoawl, endospatula and endoelevator.

25. A device according to claim 1, wherein the radial distance between the cutting edge and the inside of the wall of the cutting tool amounts to at most a quarter of the distance between the cutting edge and the outer surface of the wall.

26. A device according to claim 1, wherein the cutting edge coincides with the end of the inside of the wall of the cutting tool.

27. A device according to claim 1, wherein the cavity of the cutting tool has an internal diameter of between 3.2 mm and 6.1 mm.

28. A device according to claim 10, wherein the cutting edge is of serrated construction.

29. A method for minimally invasive intervention in the region of the spinal column, the method comprising at least the following steps:
   providing a cutting tool comprising an element in the form of a hollow cannula, said hollow cannula comprising a cutting edge at a distal end thereof, said distal end defining a single opening, said opening at said distal end is generally bevelled in shape relative to a longitudinal axis of symmetry of the element, said cannula comprising a cavity, said single opening extending over an entire cross section of said cavity, said cutting edge extending predominantly in a direction perpendicular to said longitudinal axis of said element;
   at least one rod is brought percutaneously with its distal end at least as far as into the intervention region;
   introducing said hollow cannula at least as far as into the intervention region around an outside of said rod, and by movement relative to said rod;
   introducing an endoscope movably through the hollow cannula;
   moving said cannula to have said cutting edge perform cutting of the intervention area, said moving and said cutting being performed when said cannula is around said outside of said one of said rod and said endoscope.

30. A method according to claim 29, wherein the cutting tool is swivelled over a limited angular range.

31. A method according to claim 30, wherein the cutting tool is swivelled over an angular range of up to 30°, preferably of less than 12°.

32. A method according to claim 29, wherein an anchoring tool is inserted through the working cavity of an endoscope introduced as far as into the spinal column region and is anchored in the region of the posterior longitudinal ligament.

33. A method according to claim 32, wherein an endoawl is introduced as the anchoring tool and is percussively anchored axially with its sharp tip in the area on the posterior longitudinal ligament or adjacent areas of bone.

34. A method according to claim 32, wherein an endospatula with flattened distal end is introduced as the anchoring and is anchored between the posterior longitudinal ligament and bone by axial application of force.

35. A method according to claim 32, wherein an endoelevator with a thickened portion at the distal end provided with an undercut is introduced as the anchoring tool and is anchored between bone and the posterior longitudinal ligament against the latter under tension.

36. A method according to claim 32, wherein a milling chisel is introduced over the anchoring tool, acting as guide tool, and the bone material to be removed is removed therewith by at least one swivelling movement of the milling chisel.

37. A method according to claim 36, wherein the milling chisel is rotated.

38. A method according to claim 36, wherein the milling chisel is moved axially in cycles.

39. A method according to claim 36, wherein the milling chisel is moved by a motor.

40. A device in accordance with claim 1, wherein:
said cutting edge extends in a circumferential direction of said longitudinal axis of said hollow cannula.

41. A device in accordance with claim 1, wherein:
said direction of said cutting edge is arranged to not intersect said longitudinal axis.

42. A device in accordance with claim 1, wherein:
said distal end forms only one said opening which is in communication with said cavity.

43. A device in accordance with claim 42, wherein:
said cutting edge is arranged at farthest distal position of said hollow cannula.

44. A device in accordance with claim 43, wherein:
said hollow cannula has an annular wall that surrounds said cavity, said cutting edge being formed in said annular wall, said annular wall having a radially inside surface and a radially outside surface;
said cutting edge is positioned at said annular wall radially spaced from said outside surface of said annular wall.

45. A device in accordance with claim 44, wherein:
a radial distance between said cutting edge and said inside surface is less than or equal to a quarter of a radial distance between said cutting edge and said outer surface of said annular wall.

46. A device for endoscopic intervention in the skeletal region, in particular on the spinal column, the device comprising:
a cutting tool comprising an element in the form of a hollow cannula, said hollow cannula comprising a cutting edge at a distal end thereof, wherein said distal end forms only one face defining an opening, said one face and said opening being generally bevelled in shape relative to a longitudinal axis of symmetry of said element, said cannula comprising a cavity, said opening extending over an entire cross section of said cavity, said cutting edge extending predominantly in a direction perpendicular to said longitudinal axis of said element;
an optical probe (endoscope) moveably mounted in said cavity for insertion through said cavity of said cannula and out of said opening at said distal end; and
a means for moving said cutting tool relative to said optical probe, said means for moving said cutting tool brings about a cyclic swivelling movement about a longitudinal axis of symmetry of said cutting tool.

47. A device according to claim 46, wherein the cutting edge is joined to the outside of the wall of the cutting tool via a tapered surface.

48. A device according to claim 46, wherein the radial distance between the cutting edge and the inside of the wall of the cutting tool amounts to at most a quarter of the distance between the cutting edge and the outer surface of the wall.

49. A device according to claim 48, wherein the cutting edge coincides with the end of the inside of the wall of the cutting tool.

50. A device according to claim 46, further comprising an outer hollow cannula for receiving the cutting tool.

51. A device according to claim 46, wherein the means for moving the cutting tool brings about a cyclic movement about a longitudinal axis of symmetry of the cutting tool over a swivel radius of in each case up to 15°, preferably less than in each case 6° with regard to a neutral position.

52. A device according to claim 46, wherein the cavity of the cutting tool has an internal diameter of between 2.7 mm and 7.3 mm.

53. A device according to claim 46, wherein the cutting edge is of serrated construction.

54. A device according to claim 46, further comprising a milling chisel which may be inserted through the endoscope.

55. A device according to claim 54, wherein the milling chisel is of hollow-cylindrical construction.

56. A device according to claim 46, further comprising at least one anchoring tool which may be inserted through the endoscope.

57. A device according to claim 56, wherein the anchoring tool may be fixed with its distal end to the posterior longitudinal spinal ligament.

58. A device according to claim 56, wherein the anchoring tool is provided at its rear (proximal) end with a connection configuration for non-rotatable connection with a handle or the like.

59. A device according to claim 56, wherein the anchoring tool is provided in its rear area distally of the connection configuration with graduations, in particular in the form of notches extending around part of the circumference of the connection tool perpendicularly to the longitudinal axis thereof.

60. A device according to claim 56, wherein the anchoring tool is an endoawl.

61. A device according to claim 60, wherein the endoawl comprises a sharp distal tip.

62. A device according to claim 56, wherein the anchoring tool is an endospatula.

63. A device according to claim 62, wherein the endospatula is provided at its distal end with an end-face cutting edge.

64. A device according to claim 56, wherein the anchoring tool is an endoelevator.

65. A device according to claim 64, wherein the endoelevator comprises in its distal end region firstly a taper and then a thickened portion at its outermost distal end.

66. A device according to claim 56, further comprising a handle connectable to the anchoring tool.

67. A device according to claim 54, further comprising a drive, preferably a rotary drive, in particular a rotary drive with chiselling action for the milling chisel.

68. A device according to claim 54, further comprising at least two of the following anchoring tools: endoawl, endospatula and endoelevator.

69. A device according to claim 46, wherein the radial distance between the cutting edge and the inside of the wall of the cutting tool amounts to at most a quarter of the distance between the cutting edge and the outer surface of the wall.

70. A device according to claim 46, wherein the cutting edge coincides with the end of the inside of the wall of the cutting tool.

71. A device according to claim 46, wherein the cavity of the cutting tool has an internal diameter of between 3.2 mm and 6.1 mm.

72. A device according to claim 54, wherein the cutting edge is of serrated construction.

73. A device according to claim 46, wherein:
said cutting edge extends in a circumferential direction of said longitudinal axis of said hollow cannula.

74. A device according to claim 46, wherein:
said direction of said cutting edge is arranged to not intersect said longitudinal axis.

75. A device according to claim 46, wherein:
said distal end forms only one said opening which is in communication with said cavity.

76. A device according to claim 75, wherein:
said cutting edge is arranged at farthest distal position of said hollow cannula.

77. A device according to claim 76, wherein:
said hollow cannula has an annular wall that surrounds said cavity, said cutting edge being formed in said annular wall, said annular wall having a radially inside surface and a radially outside surface;
said cutting edge is positioned at said annular wall radially spaced from said outside surface of said annular wall.

78. A device according to claim 77, wherein:
a radial distance between said cutting edge and said inside surface is less than or equal to a quarter of a radial distance between said cutting edge and said outer surface of said annular wall.

* * * * *